United States Patent
Russell

(10) Patent No.: US 6,493,581 B2
(45) Date of Patent: Dec. 10, 2002

(54) SYSTEM AND METHOD FOR RAPID RECRUITMENT OF WIDELY DISTRIBUTED EASILY OPERATED AUTOMATIC EXTERNAL DEFIBRILLATORS

(75) Inventor: James K. Russell, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 24 days.

(21) Appl. No.: 09/749,618

(22) Filed: Dec. 28, 2000

(65) Prior Publication Data

US 2002/0087194 A1 Jul. 4, 2002

(51) Int. Cl.$^7$ .......................... A61B 5/26; H04M 11/04
(52) U.S. Cl. ..................... 607/5; 600/515; 379/45; 455/456
(58) Field of Search ................. 607/5, 6; 455/456; 600/515, 518; 379/38, 45

(56) References Cited

U.S. PATENT DOCUMENTS

| | | | |
|---|---|---|---|
| 5,348,008 A | * 9/1994 | Bornn et al. | 128/642 |
| 5,564,429 A | * 10/1996 | Bornn et al. | 128/696 |
| 5,593,427 A | 1/1997 | Gliner et al. | |
| 5,607,454 A | 3/1997 | Cameron et al. | |
| 5,735,879 A | 4/1998 | Gliner et al. | |
| 5,752,976 A | * 5/1998 | Duffin et al. | 607/32 |
| 5,836,993 A | 11/1998 | Cole | |
| 5,879,374 A | 3/1999 | Powers et al. | |
| 6,141,584 A | * 10/2000 | Rockwell et al. | 607/5 |
| 6,208,897 B1 | * 3/2001 | Jorgenson et al. | 607/5 |
| 6,292,687 B1 | * 9/2001 | Lowell et al. | 600/515 |
| 6,292,698 B1 | * 9/2001 | Duffin et al. | 607/32 |
| 6,312,378 B1 | * 11/2001 | Bardy | 600/300 |
| 6,328,699 B1 | * 12/2001 | Eigler et al. | 600/486 |
| 6,334,070 B1 | * 12/2001 | Nova et al. | 607/5 |
| 6,356,785 B1 | * 3/2002 | Snyder et al. | 607/5 |

* cited by examiner

Primary Examiner—John Rivell

(57) ABSTRACT

A system for rapid recruitment of automatic external defibrillators and operators of the defibrillators including a plurality of automatic external defibrillators. A locator is operable to determine locations of the defibrillators, a victim, and a potential operator of the defibrillators. A communicator is operable to communicate the location of at least one of the defibrillators to the potential operator.

27 Claims, 2 Drawing Sheets

SYSTEM AND METHOD FOR RAPID RECRUITMENT OF WIDELY DISTRIBUTED EASILY OPERATED AUTOMATIC EXTERNAL DEFIBRILLATORS

BACKGROUND OF THE INVENTION

1. Field of the Invention

The present invention relates to a system and method for locating defibrillators and potential operators of the defibrillators to administer to a victim.

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation ("VF") or shockable ventricular tachycardia ("VT") to a normal sinus rhythm. Similarly, external cardioverters can be used to provide paced shocks to convert atrial fibrillation ("AF") to a more normal heart rhythm.

Sudden cardiac arrest ("SCA") is the leading cause of unanticipated death in the United States. On average, about 600 people per day die of SCA. This translates to nearly one death every two minutes. It is likely that these statistics would, at a minimum, hold true for third world countries. Precise international statistics are not available but the U.S. rate for coronary heart disease deaths, of which sudden deaths constitute nearly half, is representative of international rates (rank $16^{th}$ and $13^{th}$ among 36 nations reported by the World Health Organization (WHO), for men and women, respectively).

Most sudden cardiac death is caused by VF, in which the heart's muscle fibers contract without coordination, thereby interrupting normal blood flow to the body. The only effective treatment for VF is electrical defibrillation, which applies an electrical shock to the patient's heart. The electrical shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. As improved access to defibrillators increases, survival rates from SCA also increase.

Currently, in a typical scenario, a witness to a victim contacts an emergency response operator, such as by dialing 911 or public service access points, to alert the operator to the existence of the victim. The emergency response operator then dispatches an emergency response team, such as firefighting teams, paramedics and emergency medical technicians (EMTs) to the site of the victim. Emergency response systems rely on notification of the operator or dispatcher and the urgent dispatch of centralized resources and highly trained personnel to the site of the victim.

The above-described system may work well in many situations.

However, given the short response time necessary to address cardiac emergencies, the currently utilized system may not provide timely response in numerous instances. For example, traffic congestion in many metropolitan areas as well as large travel distances in both in rural areas and urban areas may prevent timely response to 911 calls. For example, the probability of successfully resuscitating a victim of sudden cardiac arrest declines from approximately 90% in the first minute post-cardiac arrest to less than about 10% after about 10 minutes. Also, as time goes on, the chances of brain damage due to lack of oxygen as a result of lack of blood flow or other unfavorable affects greatly increase with increased passage of time after a cardiac arrest.

Current emergency medical response systems do not reliably respond in less than ten minutes in many environments and particularly not in high population density environments because of crowding, traffic, and/or long delays to ascend high-rise buildings, among other factors. As a result of delayed treatment, the vast majority of out of hospital sudden cardiac arrest victims die.

In some areas, implementation of publicly accessible automatic defibrillation systems provides a partial solution to delay in emergency medical response systems to treat cardiac arrest victims. The automatic defibrillation systems include automatic external defibrillators (AEDs) deployed in publicly accessible locations and capable of application by minimally trained operators or untrained lay people. Such systems typically rely on information campaigns and local signage to bring attention to the availability and location of AEDs. Publicly available defibrillators have provided some success in highly trafficked narrowly constrained areas, such as Chicago O'Hare Airport. However, success in more general areas is doubtful. Also, increasing the possibility of success in even highly trafficked areas would be desirable.

SUMMARY OF THE INVENTION

The present invention relates to a system and method that addresses the lack of knowledge of AEDs. The present invention helps to rapidly locate victims, defibrillators, and/or potential operators of the defibrillators.

A system according to the present invention rapidly recruits automatic external defibrillators and operators of the defibrillators. The system includes a locator operable to determine locations of the defibrillators, a victim, and/or a potential operator of the defibrillators. A communicator is operable to communicate the location of at least one of the defibrillators to the potential operator.

Additionally, the present invention concerns a method for rapid recruitment of automatic external defibrillators and operators of the defibrillators. According to the method, a location of a victim that could benefit from application of a defibrillator is identified. Also, location of a potential operator of the defibrillator is identified. Additionally, a location of the defibrillator for use by the potential operator is identified. The location of the defibrillator is communicated to the potential operator.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

Figure 1:
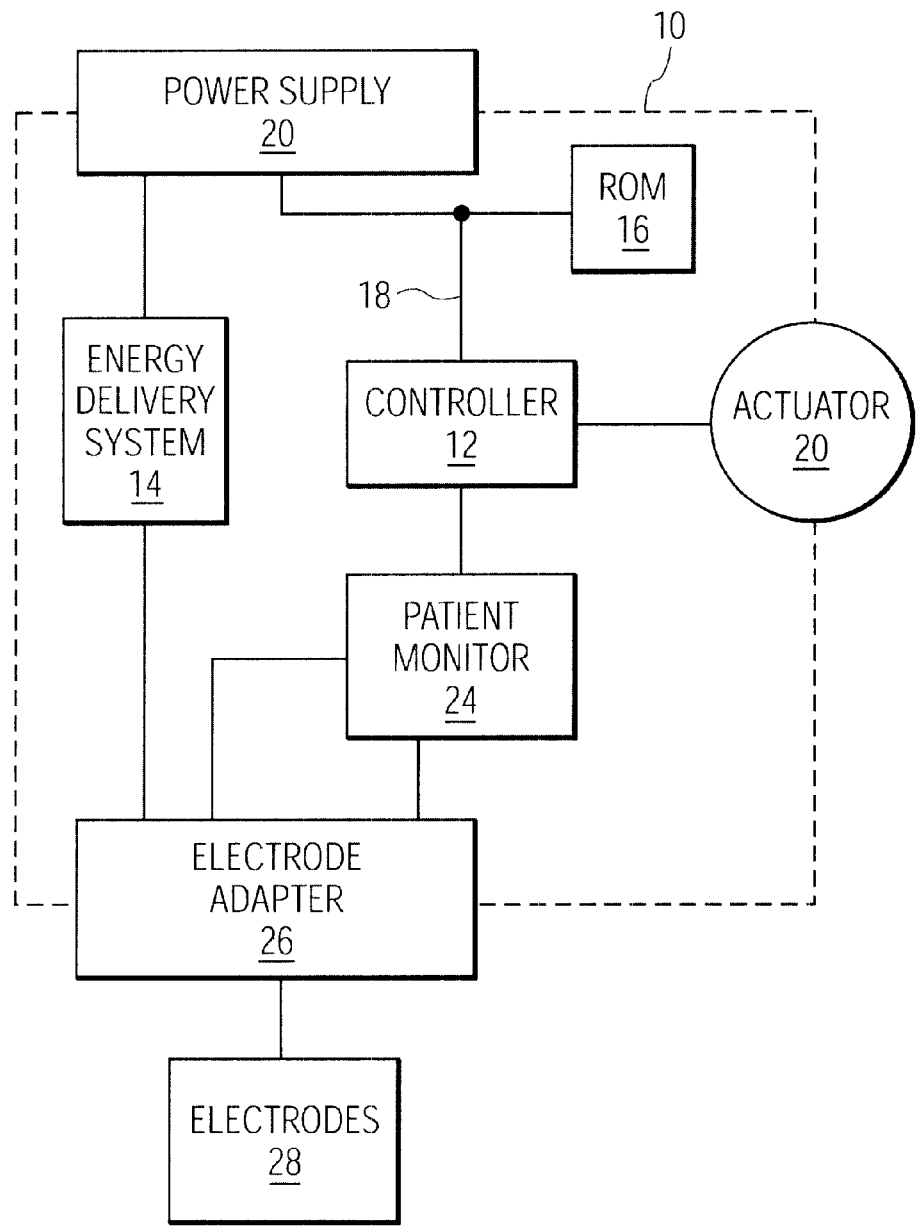
FIG. 1 represents a block diagram of an electrotherapy device showing a detachable electrode system.

By providing a system and method for rapid recruitment of AEDs, the present invention can help to decrease response times and hopefully as a result increase survivability of cardiac arrest victims and decrease complications resulting from delayed application of treatment. The present invention can help to make the existence and location of nearby AEDs known to witnesses of cardiac arrest. Even if one or many defibrillators are in the vicinity of a witness, witnesses to cardiac arrest are unlikely to know of the existence and/or location of AEDs. The present invention can solve this problem.

The present invention can also make locations of AEDs known to designated or volunteer potential operators, who may have training in the use of the AEDs. Even where such persons know locations of defibrillators, they most likely do not know of the existence or location of a victim. Emergency response operators may not know of the locations of AEDs or of nearby potential to designated or volunteer operators or a potential operator can reach an AED or victim. The present invention can address these needs as well.

By providing location and contact information concerning victims, AEDs, and/or potential operators, the present invention can effectively coordinate a response to a cardiac arrest victim. Through providing this information, the present invention can permit faster intervention to cardiac arrest victims than currently utilized systems of emergency response. With an estimated 10% increase in mortality for every minute delay in response, the difference between arrival of a potential operator to a victim in 5 minutes or less and the arrival of a trained emergency response team can be the difference between life and death of a victim.

The existence of a victim is first identified by the system. The identification may take place in a number of ways through a number of channels. A system according to the present invention includes a locator that is capable of determining locations of AEDs, victims, and/or potential operators of the defibrillators. These are the three significant elements involved in generating a quick response to a cardiac arrest victim. Which of these elements the locator locates may depend upon each emergency response situation. Along these lines, it may be desirable or necessary to only locate a defibrillator for a potential operator.

Before locating any defibrillator or operator, a victim is typically first identified. The victim is usually brought to the attention of the system through the witness calling the general emergency response phone number (911 in the United States). Whether or not the victim has suffered a cardiac arrest may be determined before or after identification of the victim. Sometimes, a witness may be able to determine that cardiac arrest has occurred. Other times, an emergency response operator will be able to instruct the witness or another party how to determine whether cardiac arrest has occurred. If there is doubt, attaching electrodes of a AED can permit the AED to monitor the victim to determine whether cardiac arrest and/or a shockable rhythm have occurred or exist.

After a victim has be en identified, an emergency medical response team may be dispatched to the victim. Upon dispatching the emergency response team, an emergency response operator may start the process of identifying defibrillators in the vicinity of a potential operator. If the potential operator is the witness then the process typically would include identifying defibrillators in the vicinity of the victim, usually the closest to the victim or most easily accessed. If the identity of the potential operator is other than the witness, then the defibrillator identified may not necessarily be the closest to the victim.

A locator according to the present invention can include a computer system. The computer system can include a processor and a storage device for storing a geographical database. The database can include data regarding location of defibrillators and potential operators. The process of identifying defibrillators may include providing the location of the victim to the computer. The computer can then analyze the relative locations of the victim, available AES and/or potential responders to determine relative positions of these elements and then how to instruct the dispatcher.

Once existence of a victim that can potentially benefit from defibrillation is identified, the location of the victim can be identified. The location can be determined in a number of ways. For example, the witness may describe the location to an emergency response operator.

Rather than rely on a verbal description of the victim's location, the system may utilize one or more communication systems to locate a victim. Along these lines, the public telephone system, whether land based or cellular based, could determine the location of the witness as the 911 operator is called. For example, enhanced 911 services currently in use in many localities can identify the address of the telephone utilized by the caller. Enhanced cellular technology could also identify the location of the caller. Additionally, a global positioning system (GPS) could be employed to identify the location of the caller. Any other system could also be utilized to locate the caller and, hence, the victim. Systems for determining locations are known in the art.

Once the location of a victim that might benefit from administration of a defibrillator is known, the location can be entered into a computer system for determining locations of defibrillators and/or potential operators. The computer system can also be considered to form part of the locator of a system according to the present invention. If the location has been determined automatically, such as through enhanced telephone system software, then the location may be entered into the computer system automatically. If the location has been determined manually through description by a witness or even if the location has been determined automatically, the location may be entered into the computer system manually.

Manual entry of the location information may be carried out in a variety of ways. For example, the computer system may display a map of an area of responsibility for an emergency response operator. The operator could use a pointing device to choose the location of the victim. Another alternative includes the operator entering the address of the location of the victim or a nearby address utilizing a keyboard or other input device that permits entry of text into a computer. Any other means for entry of the victim's location could also be utilized. Notification of an emergency medical response team could also take place after the entry of the victim location in the computer system.

After entry of the victim location in the computer system, the location information may be compared to information in a database of AED and potential operator locations. The previously created database could include locations of all AEDs and potential operators. The identity of the operator of an AED, or potential operator prior operation of the AED, may vary. The operator could be the witness to the victim. In other cases, a designated operator may act as the operator. An example of such a person could be a security guard, or a designated person on a floor of a building. Such a person could be identified and trained for potential emergency response. Alternatively, the operator may be a volunteer operator, such as a next door neighbor. The volunteer may or may not have any previous training.

After entry of the victim location, the computer system could automatically determine AEDs and/or potential operators in the vicinity of the victim. After determining locations of the AEDs and/or potential operators, the computer could generate output of the results. The output could be in one or more forms. The output could be in the form of a map that displays the location of the victim and locations of AEDs and/or potential operators. Additionally or alternatively, a list of locations of AEDs and/or potential operators could be output.

Information about the AEDs and/or potential operators could include address and contact information. The information could also include walking and/or driving directions to enable a potential operator to find an AED and/or a victim. Along these lines, AEDs and/or potential operators could be contactable through a telephone and/or paging system or through any other means. The output could be organized in order of proximity to the victim or any other order.

The output could be provided to the emergency response operator in a variety of formats. For example, the computer could display the results of the location comparison on a monitor. Additionally or alternatively, the computer system could print out the results of the comparison on a printer. Any other output means could also be utilized.

After carrying out the comparison, an emergency response operator may review the output and manually determine AEDs to direct a potential operator to and/or potential operators to contact. Alternatively, through a previously generated algorithm the computer system may locate AEDs and/or potential operators. The algorithm can take into account proximity of AEDs and potential operators to a victim. The algorithm could also take into account duty to respond, availability to respond, previous training, proximity to AEDs and/or other characteristics of a designated operator or volunteer operator. For example, a designated operator, such as a security guard, may not be on duty. According to another example, a first potential operator may be farther from a victim than a second potential operator but the total distance from the location of the first potential operator to an AED and to the victim is less for the first operator than the second. In this case, first potential operator might be contacted first. By taking into account factors other than just proximity to a victim, a potential operator farther from a victim could be contacted first.

Once AEDs and/or potential operators have been determined, potential operators can be contacted in order of priority. The computer system could contact the potential operators automatically. Alternatively, an emergency response operator could initiate contact with the potential operators or make the contact him or her self Contact with potential operators can be established in a number of ways. For example, a telephone and/or paging system could be utilized to alert potential operators. A potential operator may appear more than once in a list of potential operators generated by a computer system, not necessarily consecutive, reflecting multiple ways to reach them, such as, for example, landline, pager, cellular phone.

Once contact with a potential operator is established, a number of pieces of information could be communicated to the potential operator, including existence of a victim, location of the victim, location of AEDs, directions to the victim and/or the AEDs and/or any other information. In cases where the potential operator is the witness, then the witness does not really require any information about the location of the victim and may, instead only receive information concerning locations of AEDs.

Communicating the location of the AEDs to the potential operators may involve activating an indicator on or associated with the AEDs. Along these lines, a visual and/or audible indicator may be activated to communicate the location of the AEDs to the potential operators. For example, a light could be activated or alarm could sound to attract the potential operators. The sounding of an alarm could include a tone(s) and/or a spoken alert. The emergency response operator's voice could serve as part of the alarm. To facilitate detection of the AEDs, the indicator could be located one or more places including, for example, on an AED, near and AED, at the entrance of a room and/or building where AEDs are located.

After the potential operator and/or an AED are located, the potential operator transports the AED to a location as close as necessary to the victim as necessary to effectively operate the AED. The system may then instruct the potential operator in use of the AED. The instructions could be written and/or verbal. Written instructions could be associated with the AED. Verbal instructions could be stored in the AED and provided as needed to a potential operator. Additionally or alternatively, verbal instructions could be given by the emergency response operator or by the computer system. The AED may monitor the patient to ensure that the patient has a shockable rhythm. If it is believed that the patient could benefit from application of a shock, the potential operator may then proceed to operate the AED to deliver a defibrillating shock to the victim. Further monitoring and shocking may then be carried out if necessary. An emergency medical response team may arrive and administer to the victim.

The following discussion provides a background discussion of an AED. FIG. 1 is a block diagram showing an embodiment of a defibrillator 10. The defibrillator 10 can include a controller 12 for operating an energy delivery system 14 and for performing other aspects of the operation of the defibrillator. Software instructions for the operation of the defibrillator may be accessible from a memory device. For example, software may be stored in read only memory (ROM), such as incorporated ROM 16. Any other memory structure, such as RAM or other memory device may also be utilized. The controller may access instructions for operation from ROM 16. It should be understood that in this and other embodiments described below "controller" means a microprocessor, controller, gate array, other control logic, or any combination of these elements.

Controller 12 can communicate with ROM 16 via a memory bus 18. A recordable memory module 32 may be attached to defibrillator 10 via an electrode system 36, as shown in FIG. 1. Electrode system 36 can include electrodes 28 and an electrode adapter 26.

Electrode adapter 26 may be connected to electrodes 28 and may be removably connected to the defibrillator 10. A suitable electrode system 36 adaptable for use in this invention would be, for example, Heartstream ForeRunners® electrodes.

Electrodes 28 can communicate with a patient monitor 24 via an electrode adapter 26 to provide patient ECG data from the patient to the patient monitor 24. The electrodes include electrodes capable of delivering defibrillation, monitoring a patient condition, delivering pacing pulses, or a combination of those features. In an AED, the patient monitor 24 can monitor the patient for a heart rhythm and subsequently determine whether the monitored rhythm is shockable.

When a shockable rhythm is detected, the patient monitor 24 can then communicate a shock decision to the controller 12. Next, the controller 12 can communicate to the energy delivery system 14. Subsequently, the energy delivery system 14 can deliver a therapeutic energy pulse to the patient (not shown) through electrodes 28 attached to the defibrillator 10 via electrode adapter 26, using the power supply 20 as the energy source.

Figure 2:
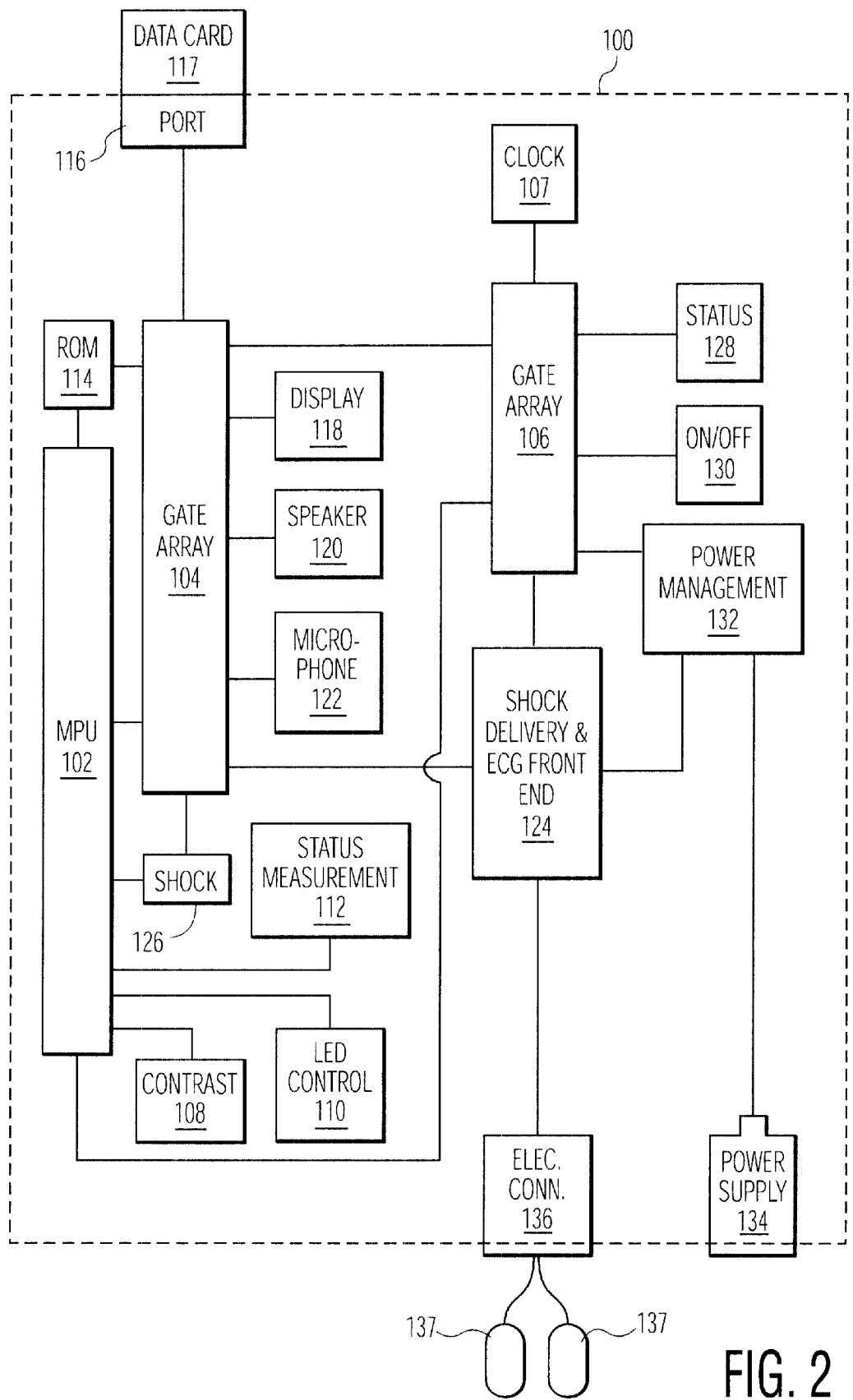
FIG. 2 represents a block diagram that illustrates major components of a semi-automatic external defibrillator shown in FIG. 1.

FIG. 2 represents a block diagram that shows major components of an AED. Further detailed information about the operation of an AED can be obtained in U.S. Pat. No. 5,836,993, to Cole, for "Electrotherapy Device Control System and Method"; and U.S. Pat. No. 5,593,427, to Gliner et al., for "Electrotherapy Method", the specifications of which are incorporated herein by reference. As will be appreciated by those of skill in the art, the invention can be used in a variety of AEDs and is not limited to this configuration, which is used for illustration purposes only.

In the device shown in FIG. 2, defibrillator control functions are divided among a microprocessor unit (MPU) 102 and two custom gate arrays 104 and 106. MPU 102 performs program steps according to software instructions provided to it from ROM 114. Also, MPU 102 controls the operation of certain buttons (such as display contrast buttons 108) and certain system LED's 110 (such as LED's associated with the shock button and the electrode connector). Additionally, MPU 102 also receives system status information as shown by block 112.

The device may include a gate array 104 for implementing the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 can provide a system monitor function by performing automatic self-tests of the defibrillator and its components. Also, the gate array 106 can display the operational status of the defibrillator on a status display 128. Details of suitable self-tests may be found in U.S. Pat. No. 5,879,374, to Powers et al., for "External Defibrillator with Automated Self-Testing Prior to Use", the specification of which is incorporated herein by reference.

In addition to the above, gate array 106 may also act as the defibrillator's interface by including a user-activated on/off switch 130. Furthermore, gate array 106 can control the power management subsystem 132 to provide power to operate system components from power supply 134 and to provide energy to the shock delivery system's capacitor(s) for a therapeutic shock during treatment mode. Still further, gate array 106 may interface with the defibrillator's ECG front end and enable the shock delivery system to deliver a shock in response to detection of a patient ECG pattern requiring treatment (and actuation of the shock button). Also, gate array 106 may control delivery of the shock to electrode connector 136 in response to shock delivery status information obtained during delivery of the shock. Further information regarding this last function may be found in U.S. Pat. No. 5,735,879, to Gliner et al., for "Electrotherapy Method for External Defibrillators"; and U.S. Pat. No. 5,607,454, to Cameron et al., for "Electrotherapy Method and Apparatus"; the specifications of both which are incorporated herein by reference.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. Additionally, the operational characteristics of the defibrillator in any one of the modes can be changed as described below in greater detail.

Operation of the external defibrillator of the embodiment shown in FIG. 2 commences with the insertion of a power supply 134 or user activation of the power on button. Once gate array 106 confirms that a power supply 134 is inserted, gate array 104 may prompt MPU 102 to begin its boot sequence. The boot sequence can begin with MPU 102 sending out a series of addresses to power supply 134.

As is known in the art, while in patient treatment mode, a defibrillator, such as defibrillator 100, typically performs the following functions:

(1) determine whether electrodes 137 are attached to electrode connector 136;

(2) receive ECG information from a patient through such electrodes;

(3) analyze the ECG information to determine whether a therapeutic shock is advised; and (4) deliver a shock to the patient through the electrodes 137 if a shock is advised and if the shock button 126 is actuated by a user.

It is important to realize that FIGS. 1 and 2 only illustrate one possible embodiment of a defibrillator and that any other embodiment of a defibrillator may be utilized in conjunction with the present invention.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed:

1. A system for rapid recruitment of automatic external defibrillators and operators of the defibrillators, the system comprising:

a locator operable to determining locations of the defibrillators, a victim, and a potential operator of the defibrillators based on predetermined criteria; and a communicator operable to communicate the location of at least one of the defibrillators to the potential operators.

2. The system according to claim 1, wherein the locator comprises a communication system including at least one of a wired communication system or a wireless communication system.

3. The system according to claim 2, wherein the system automatically determines the location of the victim as the communication system is utilized by a witness to the victim to alert an emergency response dispatcher of the existence of the victim.

4. The system according to claim 2, wherein the communication system is utilized by a witness to the victim to alert an emergency response dispatcher of the existence of the victim and the location of the victim is described by the witness.

5. The system according to claim 1, wherein the locator comprises a database including at least one location information for the defibrillators and the potential operators.

6. The system according to claim 5, wherein the locator further comprises a processor for locating defibrillators in the vicinity of the potential operator and at least one of a display for displaying and a printer for printing the location of the victim and at least one of locations of the defibrillators and locations of potential operators.

7. The system according to claim 6, wherein the processor or the emergency response operator identifies defibrillators in the vicinity of the potential operator.

8. The system according to claim 1, wherein the communicator comprises connections of the defibrillators to a communication system and at least one of a visual and an audible alarm associated with each defibrillator, wherein the alarm is activated through the communication system.

9. The system according to claim 8, wherein the communicator activates the alarm in a sequence starting with a defibrillator nearest to the victim.

10. The system according to claim 8, wherein the communicator activates the alarm in a sequence starting with a defibrillator nearest to the potential operator.

11. The system according to claim 1, wherein the locator determines a location of a designated or volunteer operator based upon at least one of proximity to the victim, proximity to an available defibrillator, duty to respond and availability to respond.

12. The system according to claim 1, further comprising: an instruction system for instructing the potential operator to use the defibrillator.

13. The system according to claim 1, further comprising: means for notifying an emergency medical response team of the existence of the victim.

14. The system according to claim 2, wherein the defibrillators are connected to the communication system.

15. A method for rapid recruitment of automatic external defibrillators and operators of the defibrillators, the method comprising:

identifying a location of a victim that could benefit from application of a defibrillator;

identifying a location of a potential operator of the defibrillator based on predetermined criteria;

identifying a location of the defibrillator for use by the potential operator; and communicating the location of the defibrillator to the potential operator.

16. The method according to claim 15, wherein the location at least one of the victim, the potential operator, and the defibrillator is determined through a communication system comprising at least one of a wireless communication system and a wired communication system.

17. The method according to claim 15, wherein identifying a location of at least one of the victim, the potential operator, and the defibrillator comprises comparing the location of the potential operator with a database comprising location information for the defibrillators to determine defibrillators in the vicinity of the potential operator.

18. The method according to claim 17, wherein a processor automatically carries out the comparison.

19. The method according to claim 15, further comprising determining a potential operator in the vicinity of the victim and alerting the potential operator of the existence of the victim.

20. The method according to claim 15, further comprising at least one of displaying and printing out the location of the victim and at least one of potential operators and the defibrillators, wherein the emergency response operator manually identifies potential operators by viewing the display.

21. The method according to claim 15, wherein the potential operator is located remote from the victim and is alerted to the existence of the victim through at least one of a telephone system and a paging system.

22. The method according to claim 15, wherein the location of the defibrillator is communicated by activating at least one of a visual and audible alarm.

23. The method according to claim 15, further comprising:

alerting the potential operator of the existence and location of the victim; and directing the potential operator to a defibrillator.

24. The method according to claim 15, wherein the location of the defibrillator is communicated to the potential operator by an emergency response operator.

25. The method according to claim 15, further comprising:

alerting an emergency medical response team to the existence of the victim at least one of prior to, simultaneously with, and after identifying the location of the victim that could benefit from the application of the defibrillators.

26. The method according to claim 15, further comprising:

applying a defibrillating shock to the victim with the defibrillator.

27. The method according to claim 15, further comprising:

instructing the potential operator in the use of the defibrillator.

* * * * *